United States Patent [19]
Chen et al.

[11] Patent Number: 5,545,120
[45] Date of Patent: Aug. 13, 1996

[54] ENDOSCOPIC VIEWING SYSTEM FOR MAINTAINING A SURGEON'S NORMAL SENSE OF KINESTHESIA DURING ENDOSCOPIC SURGERY REGARDLESS OF THE ORIENTATION OF THE ENDOSCOPE VIS-A-VIS THE SURGEON

[75] Inventors: David T. Chen, Somerville, Mass.;
Steven D. Pieper, Thetford Center, Vt.;
Michael McKenna, Cambridge, Mass.

[73] Assignee: Medical Media Systems, West Lebanon, N.H.

[21] Appl. No.: 374,126

[22] Filed: Jan. 18, 1995

[51] Int. Cl.⁶ .............................. A61B 1/04; H04N 7/18; H04N 9/74
[52] U.S. Cl. ........................ 600/117; 600/103; 600/921; 348/65; 348/583; 348/61
[58] Field of Search ...................... 600/103, 117, 600/145, 921; 128/653.1, 903, 899; 606/130; 348/36, 39, 65, 61, 82, 116, 114, 142, 147, 169, 140, 583; 382/295, 296, 297, 293

[56] References Cited

U.S. PATENT DOCUMENTS

| | | | |
|---|---|---|---|
| 5,230,623 | 7/1993 | Guthrie et al. | 128/774 |
| 5,329,310 | 7/1994 | Liliegren et al. | 348/147 |
| 5,384,594 | 1/1995 | Sieber et al. | 348/169 |
| 5,417,210 | 5/1995 | Funda et al. | 348/65 |

*Primary Examiner*—Joe Cheng
*Assistant Examiner*—John P. Leubecker
*Attorney, Agent, or Firm*—Pandiscio & Pandiscio

[57] ABSTRACT

An endoscopic viewing system for maintaining a surgeon's normal sense of kinesthesia during endoscopic surgery regardless of the orientation of the endoscope vis-a-vis the surgeon.

12 Claims, 7 Drawing Sheets

ENDOSCOPIC VIEWING SYSTEM FOR MAINTAINING A SURGEON'S NORMAL SENSE OF KINESTHESIA DURING ENDOSCOPIC SURGERY REGARDLESS OF THE ORIENTATION OF THE ENDOSCOPE VIS-A-VIS THE SURGEON

FIELD OF THE INVENTION

This invention relates to endoscopic viewing systems in general and, more particularly, to endoscopic viewing systems for maintaining a surgeon's normal sense of kinesthesia during endoscopic surgery regardless of the orientation of the endoscope vis-a-vis the surgeon.

BACKGROUND OF THE INVENTION

In endoscopic surgical procedures, relatively narrow surgical instruments are inserted into the patient's body so that the distal (i.e., working) ends of the instruments are positioned at a remote interior site, while the proximal (i.e., handle) ends of the instruments remain outside the patient's body. The surgeon then manipulates the proximal handle ends of the instruments as required so as to cause the distal working ends of the instruments to carry out the desired surgical procedure at the remote interior site.

In order to visualize what is taking place at the remote interior site, the surgeon also inserts an endoscope into the body during the endoscopic surgery, together with an appropriate source of illumination.

The endoscope generally comprises an elongated shaft having a distal end and a proximal end, and at least one internal passageway extending between the distal end and the proximal end. Image capturing means are disposed at the distal end of the shaft and extend through the shaft's at least one internal passageway, whereby the image capturing means can capture an image of a selected region located substantially adjacent to the distal end of the shaft and convey that image to the proximal end of the shaft. Viewing means are in turn disposed adjacent to the proximal end of the shaft, whereby the image obtained by the image capturing means can be conveyed to a display device which is viewed by the surgeon.

The image capturing means and the viewing means commonly utilize one of several different arrangements to capture an image at the distal end of the shaft and to present it to the surgeon.

For example, in one arrangement, the image capturing means comprise a bundle of fiber optic filaments which extend through the shaft's at least one internal passageway. A lens is positioned at the distal end of the shaft to focus the desired image onto the distal end of the fiber optic bundle. The fiber optic bundle then conveys the captured image to the proximal end of the shaft, where it is received by the viewing means. In this arrangement, the viewing means may comprise a display device which is in the form of a conventional optical viewer or eyepiece which is viewed directly by the surgeon. Alternatively, and more relevant to the present invention, the viewing means can comprise an appropriate image sensor, e.g. a charge coupled device ("CCD") element or video tube, which can receive the captured image from the proximal end of the fiber optic bundle and generate corresponding video signals which are representative of the captured image. These video signals are then displayed on an appropriate display device (e.g. a monitor) which is viewed by the surgeon.

In a second arrangement, the image capturing means comprise a CCD element which is disposed at the distal end of the shaft, and wires which extend through the shaft's at least one internal passageway. An appropriate lens focuses the desired image onto the CCD element's light-receiving surface, and the wires convey the CCD element's video output signals to the proximal end of the shaft. These video signals are then displayed on an appropriate display device (e.g. a monitor) which is viewed by the surgeon.

In a third arrangement, the image capturing means comprise a so-called rod-lens system. In this embodiment, a series of rod lens elements are arranged within the shaft's at least one internal passageway so as to capture the desired image at the distal end of the shaft and convey that image to the viewing means located at the proximal end of the shaft. With this arrangement, the viewing means can comprise a display device in the form of a conventional optical viewer or eyepiece which is viewed directly by the surgeon. Alternatively, and more relevant to the present invention, the viewing means can comprise an appropriate image sensor, e.g. a charge coupled device ("CCD") element or video tube, which can receive the captured image from the proximal end of the rod-lens system and generate corresponding video signals which are representative of the captured image. These video signals are then displayed on an appropriate display device (e.g. a monitor) which is viewed by the surgeon.

Regardless of the particular construction involved, all prior art endoscopic viewing systems tend to suffer from one significant deficiency. In particular, all prior art endoscopic viewing systems suffer from the fact that, in some situations, the surgeon's normal sense of kinesthesia will be lost while observing the endoscopic surgical procedure through an endoscope.

Figure 1:
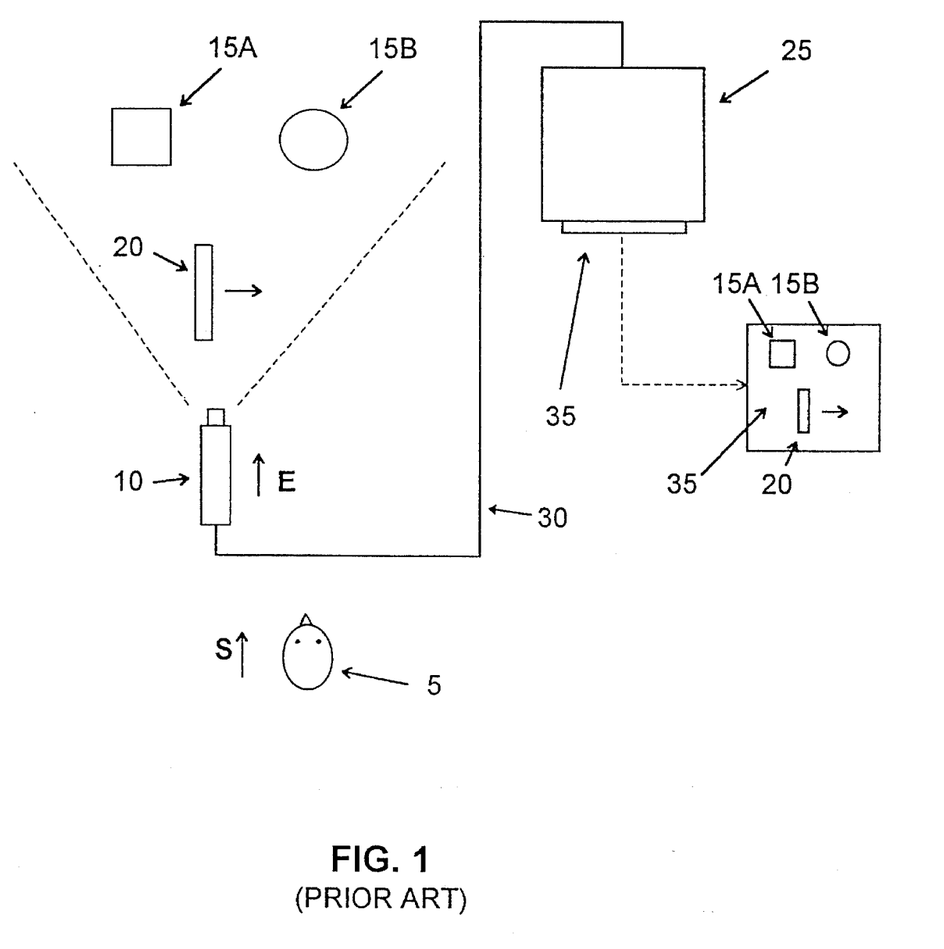
FIG. 1 is a schematic view showing an endoscopic viewing system formed in accordance with the prior art, wherein the endoscope and the surgeon are both oriented in substantially the same direction.

More particularly, and looking now at FIG. 1, during a typical endoscopic procedure, a surgeon 5 uses an endoscope 10 to view various objects (e.g. the body structures 15A and 15B and the surgical instrument 20) which are located at the remote interior site. To this end, endoscope 10 is typically connected to a monitor 25 by wires 30 such that the monitor's screen 35 will display an image of body structures 15A and 15B and surgical instrument 20 which are located at the remote surgical site.

In the situation shown in FIG. 1, body structure 15A resides to the surgeon's left and body structure 15B resides to the surgeon's right. Furthermore, as the surgeon moves surgical instrument 20 left to right through the surgical site, the surgical instrument will move away from body structure 15A and toward body structure 15B.

In a corresponding fashion, when the surgeon views the surgical site on the monitor's screen 35, the surgeon will see body structure 15A to the left and body structure 15B to the right. In addition, as the surgeon moves surgical instrument 20 from left to right across the surgical site, surgical instrument 20 will appear to move from left to right on the monitor's screen 35. Thus there is a proper correspondence between the surgeon's physical sense and what the surgeon sees on screen 35. This proper correspondence occurs because, in the situation shown in FIG. 1, surgeon 5 and endoscope 10 both face in substantially the same direction. As a result, the surgeon's normal sense of kinesthesia (i.e., the proper correspondence between tactile sense and visual sense) is effectively maintained by the endoscopic viewing system during the surgical procedure.

Figure 2:
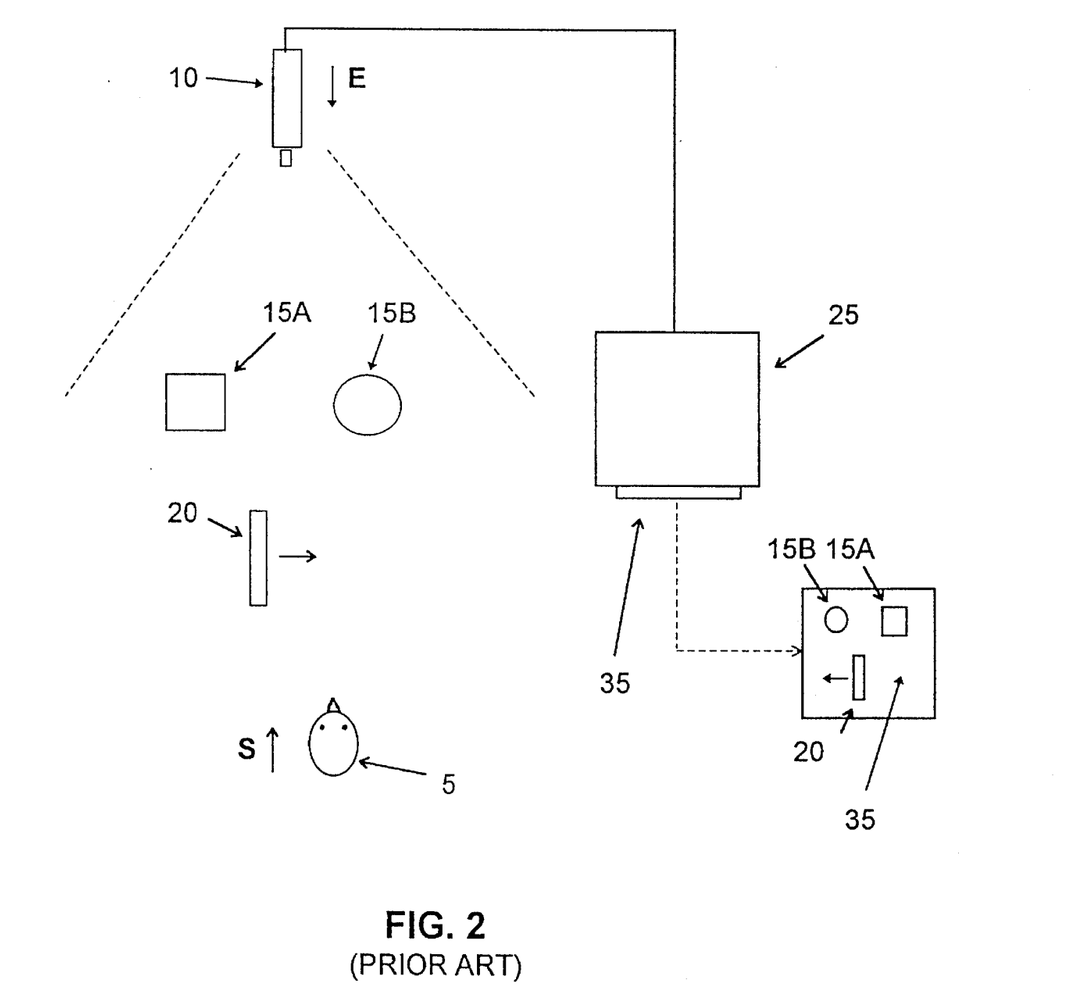
FIG. 2 is a view similar to that of FIG. 1, except that the endoscope and the surgeon are shown oriented in substantially opposite directions.

A somewhat different situation is shown in FIG. 2. Here, the position of surgeon 5 has remained the same relative to the surgical site, but the position of endoscope 10 has changed. As a result, surgeon 5 and endoscope 10 now face in substantially opposite directions. From the surgeon's physical perspective, body structure 15A still resides to the surgeon's left and body structure 15B still resides to the surgeon's right. Furthermore, as the surgeon moves surgical instrument 20 from left to right through the surgical site, the surgical instrument will still be moving away from body structure 15A and toward body structure 15B.

Unfortunately, this is not what appears on the monitor's screen 35. Instead, when the surgeon views the surgical site on the monitor's screen 35, the surgeon will see body structure 15A to the right and body structure 15B to the left. In addition, as the surgeon moves surgical instrument 20 from left to right in real space, the surgical instrument will appear to move from right to left on the monitor's screen 35. Thus there is no longer a proper correspondence between the surgeon's physical sense and what the surgeon sees on screen 35. This is because, in the situation shown in FIG. 2, surgeon 5 and endoscope 10 face in substantially opposite directions. As a result, the surgeon's normal sense of kinesthesia is not maintained by the endoscopic viewing system during the surgical procedure.

It is well recognized that the loss of the surgeon's normal sense of kinesthesia can cause the surgeon to become confused or disoriented during a surgical procedure. As a result, the procedure may take longer for the surgeon to perform. In some cases, this confusion or disorientation may actually result in the procedure being conducted improperly, possibly with some unintended harm occurring to the patient. Thus it has also been well recognized that, ideally, surgeon 5 and endoscope 10 should both always face in substantially the same direction, in the manner shown in FIG. 1. In this way the surgeon's normal sense of kinesthesia will always be maintained by the endoscopic viewing system during the surgical procedure.

Unfortunately, it has also been found that this is not always possible. In many cases, the orientation of the surgeon and the orientation of the endoscope may be dictated by other considerations. For example, when performing surgery on the interior of a joint, the patient's anatomy may dictate the number and location of the various entry portals so as to minimize damage to nerves, blood vessels, ligaments and the like. The number and location of these entry portals may not permit the surgeon and the endoscope to both face in substantially the same direction. Furthermore, in many cases, the orientation of the surgeon and the orientation of the endoscope may need to change several times during the surgical procedure so as to afford the desired approaches. Thus it will be seen that, in many cases, surgeon 5 and endoscope 10 may well end up facing in substantially opposite directions, in the manner shown in FIG. 2. As noted above, when this occurs, the surgeon's normal sense of kinesthesia will not be maintained by the endoscopic viewing system during the surgical procedure, with potentially disastrous results.

Analogous problems exist in many other fields as well. More particularly, numerous situations exist where an operator must perform tasks at a remote site using extended tools, with the operator visualizing the procedure indirectly through a remote viewing system. Examples of such fields might include nuclear material handling, toxic chemical handling, infectious material handling, closed pipeline work and remote robotic work, among many others. In all of these cases, the orientation of the operator may differ significantly from the orientation of the viewing system during some or all of the procedure, so that the operator's normal sense of kinesthesia may not be maintained by the viewing system during the remote procedure. This can result in the operator becoming disoriented or confused during the procedure. As a consequence, the procedure can take longer to complete, and/or the operator may make potentially serious errors during the procedure.

OBJECTS OF THE INVENTION

Accordingly, one object of the present invention is to provide an endoscopic viewing system which will maintain a surgeon's normal sense of kinesthesia during endoscopic surgery regardless of the orientation of the endoscope vis-a-vis the surgeon.

Another object of the present invention is to provide an endoscopic viewing system which comprises means for tracking the relative orientation between the surgeon and the endoscope, and means for processing the image captured by the endoscope prior to presentation to the surgeon, whereby the surgeon's normal sense of kinesthesia will be maintained during endoscopic surgery regardless of the orientation of the endoscope vis-a-vis the surgeon.

And another object of the present invention is to provide an endoscopic viewing system which comprises means for determining the orientation of the surgeon, means for determining the orientation of the endoscope, and means for processing the image captured by the endoscope prior to presentation to the surgeon, whereby the surgeon's normal sense of kinesthesia will be maintained during endoscopic surgery regardless of the orientation of the endoscope vis-a-vis the surgeon.

Still another object of the present invention is to provide an endoscopic viewing system which is adapted to modify the image captured by the endoscope prior to presentation to the surgeon whenever the surgeon and the endoscope are oriented in substantially different directions, whereby the surgeon's normal sense of kinesthesia will be maintained during endoscopic surgery regardless of the orientation of the endoscope vis-a-vis the surgeon.

Yet another object of the present invention is to provide an endoscopic viewing system which is adapted to rotate the image captured by the endoscope about an axis prior to presentation to the surgeon whenever the surgeon and the endoscope are oriented in substantially different directions, whereby the surgeon's normal sense of kinesthesia will be maintained during endoscopic surgery regardless of the orientation of the endoscope vis-a-vis the surgeon.

And another object of the present invention is to provide an endoscopic viewing system which is adapted to flip the image captured by the endoscope about an axis prior to presentation to the surgeon whenever the surgeon and the endoscope are oriented in substantially opposite directions, whereby the surgeon's normal sense of kinesthesia will be maintained during endoscopic surgery regardless of the orientation of the endoscope vis-a-vis the surgeon.

And still another object of the present invention is to provide an endoscopic viewing system which is adapted to rotate the image captured by the endoscope about an axis prior to presentation to the surgeon, with the degree of rotation being determined by the relative orientation of the endoscope vis-a-vis the surgeon, whereby the surgeon's normal sense of kinesthesia will be maintained during endoscopic surgery regardless of the orientation of the endoscope vis-a-vis the surgeon.

And yet another object of the present invention is to provide a remote viewing system of the sort used by an operator to visualize a remote site, whereby the viewing system will maintain the operator's normal sense of kinesthesia during the visualization regardless of the orientation of the viewing system vis-a-vis the operator.

And yet another object of the present invention is to provide a remote viewing system of the sort used by an operator to visualize a procedure being conducted by that operator at a remote site using extended tools, whereby the viewing system will maintain the operator's normal sense of kinesthesia during the procedure regardless of the orientation of the viewing system vis-a-vis the operator.

And another object of the present invention is to provide an improved viewing system which is adapted to help maintain a viewer's normal sense of kinesthesia with respect to the real world.

Still another object of the present invention is to provide an improved method for viewing an object at a remote location using a viewing system.

SUMMARY OF THE INVENTION

These and other objects of the present invention are addressed by the provision and use of a novel endoscopic viewing system which comprises:

an endoscope for capturing a first image of an object and for generating first video signals representative of the first image;

tracking means for tracking the relative orientation between the endoscope and the surgeon and for generating tracking signals representative of the relative orientation between the endoscope and the surgeon;

signal processing means connected to the endoscope and the tracking means, the signal processing means being adapted to receive the first video signals from the endoscope and modify the same as required based on the tracking signals received from the tracking means so as to provide second video signals representative of a second image of the object, wherein the second image of the object is arranged so as to maintain the surgeon's normal sense of kinesthesia during endoscopic surgery regardless of the orientation of the endoscope vis-a-vis the surgeon; and display means connected to the signal processing means for receiving the second video signals from the signal processing means and displaying the second image for viewing by the surgeon.

In one preferred embodiment of the invention, the signal processing means are arranged so that whenever the endoscope and the surgeon are oriented in substantially opposite directions, the signal processing means will simply flip the first image of the object about an axis when creating the second image of the object, whereby the second image of the object will be a mirror image of the first image of the object.

In another preferred embodiment of the invention, the signal processing means are arranged so that they will create the second image of the object by rotating the first image of the object about an axis, with the degree of rotation being determined by the relative orientation of the endoscope vis-a-vis the surgeon.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Looking next at FIGS. 3–5, a first preferred embodiment of the invention will now be described.

Figure 3:
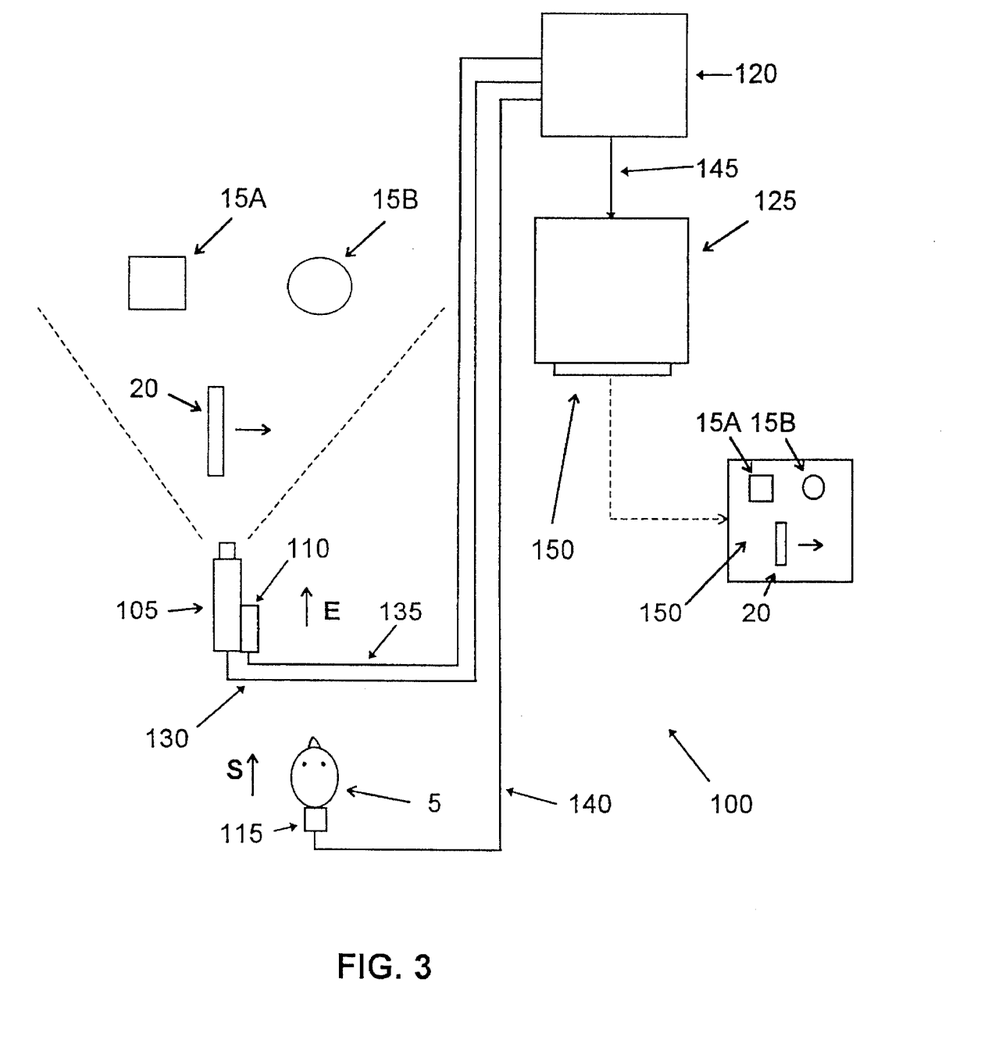
FIG. 3 is a schematic view showing a novel endoscopic viewing system formed in accordance with the present invention.

More particularly, and looking now at FIG. 3, a surgeon 5 is shown using an endoscopic viewing system 100 to view various objects (e.g. the body structures 15A and 15B and the surgical instrument 20) which are located at a remote surgical site. Endoscopic viewing system 100 is formed in accordance with the present invention and generally comprises an endoscope 105, endoscope tracking means 110, surgeon tracking means 115, signal processing means 120, and display means 125.

Endoscope 105 is an endoscope of the sort well known in the art. More particularly, endoscope 105 is of the sort which comprises (i) a lens arrangement which is disposed at the distal end of the endoscope for capturing an image of a selected region located substantially adjacent to the distal end of the endoscope, and (ii) an appropriate image sensor, e.g. a charge coupled device ("CCD") element or video tube, which is positioned on the endoscope so as to receive an image captured by the lens arrangement and to generate corresponding video signals which are representative of the captured image. Wires 130 are provided to convey these video signals to signal processing means 120.

Endoscope tracking means 110 are also of the sort well known in the art. More particularly, endoscope tracking means 110 may comprise any one of the many different tracking systems adapted to monitor the orientation of an object and to generate output signals which are representative of the orientation of that object. By way of example, endoscope tracking means 110 might comprise an articulated linkage, a tracking frame, electromagnetic sensors, ultrasonic rangefinders and/or imaging devices, among other alternatives. Endoscope tracking means 110 could be automatic, or they could be manual, e.g. they could be operated by moving a mouse, etc. Endoscope tracking means 110 are configured such that the output signals generated by endoscope tracking means 110 will be representative of the orientation of endoscope 105. Wires 135 are provided to convey these output signals to signal processing means 120.

Surgeon tracking means 115 are also of the sort well known in the art. More particularly, surgeon tracking means 115 may comprise any one of the many different tracking systems adapted to monitor the orientation of an object and to generate output signals which are representative of the orientation of that object. By way of example, surgeon tracking means 115 might comprise electromagnetic sensors, ultrasonic rangefinders and/or imaging devices, among other alternatives. Surgeon tracking means 115 could be automatic, or they could be manual, e.g. they could be operated by moving a mouse, etc. Surgeon tracking means 115 are configured such that the output signals generated by surgeon tracking means 115 will be representative of the orientation of surgeon 5. Wires 140 are provided to convey these output signals to signal processing means 120.

Signal processing means 120 are connected to endoscope 105, endoscope tracking means 110 and surgeon tracking means 115 as described above. Signal processing means 120 are adapted to receive the video output signals generated by endoscope 105 and to modify the same as required, based on the output signals of endoscope tracking means 110 and surgeon tracking means 115. More particularly, signal processing means 120 are adapted to provide video output signals which are representative of a second image of an object which is being viewed by the endoscope, wherein the second image of the object is arranged so as to maintain a surgeon's normal sense of kinesthesia during endoscopic surgery regardless of the orientation of the endoscope vis-a-vis the surgeon. To this end, signal processing means 120 may comprise an appropriately configured and/or programmed digital computer, as will hereinafter be described in further detail. Wires 145 are provided to convey the output signals from signal processing means 120 to display means 125.

Display means 125 are of the sort well known in the art. More particularly, display means 125 may comprise any one of the many different video monitors adapted to receive video signals representative of an image of an object and to display that image on a screen 150 for viewing by an observer. By way of example, display means 125 might comprise a television type monitor of the sort shown in the drawings, or they might comprise a head-mounted display, a boom-mounted unit, or any other device suitable for displaying an image from the video signals received from signal processing means 120. To the extent that display means 125 comprise a freestanding box-like enclosure, it is preferred that the display means include a pivoting base whereby the monitor can be turned to face a surgeon regardless of the surgeon's position relative to the monitor.

Figure 4:
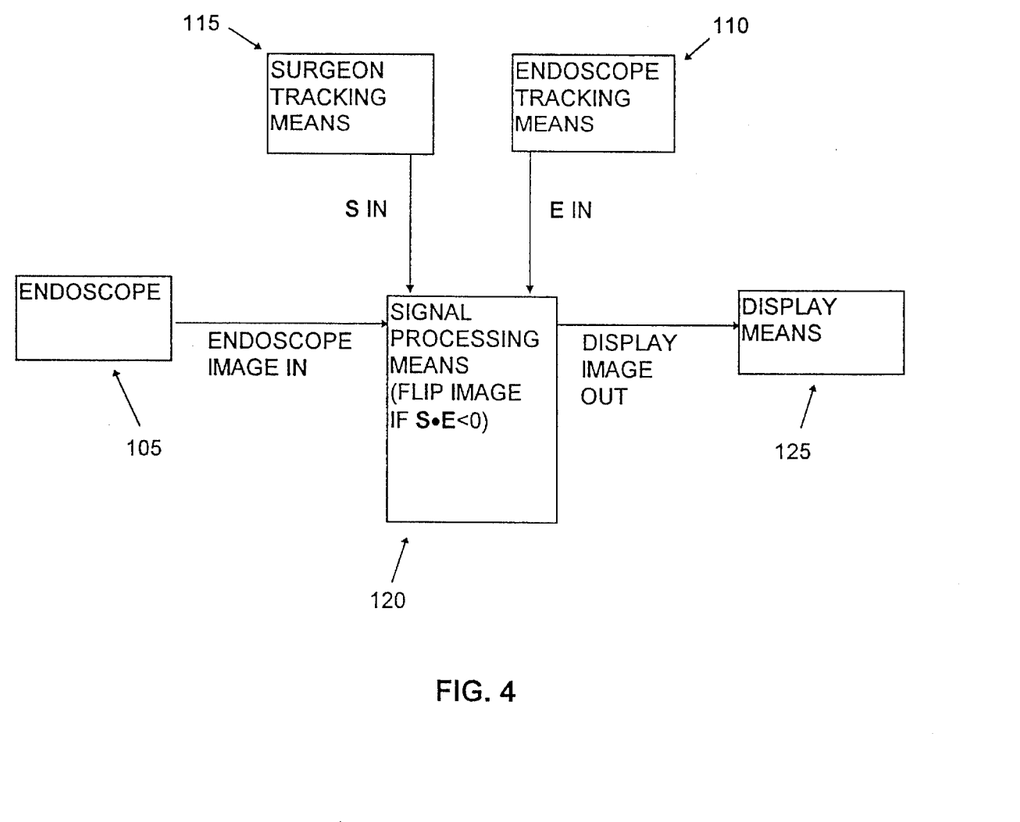
FIG. 4 is a block diagram of the novel endoscopic viewing system shown in FIG. 3.
Figure 5:
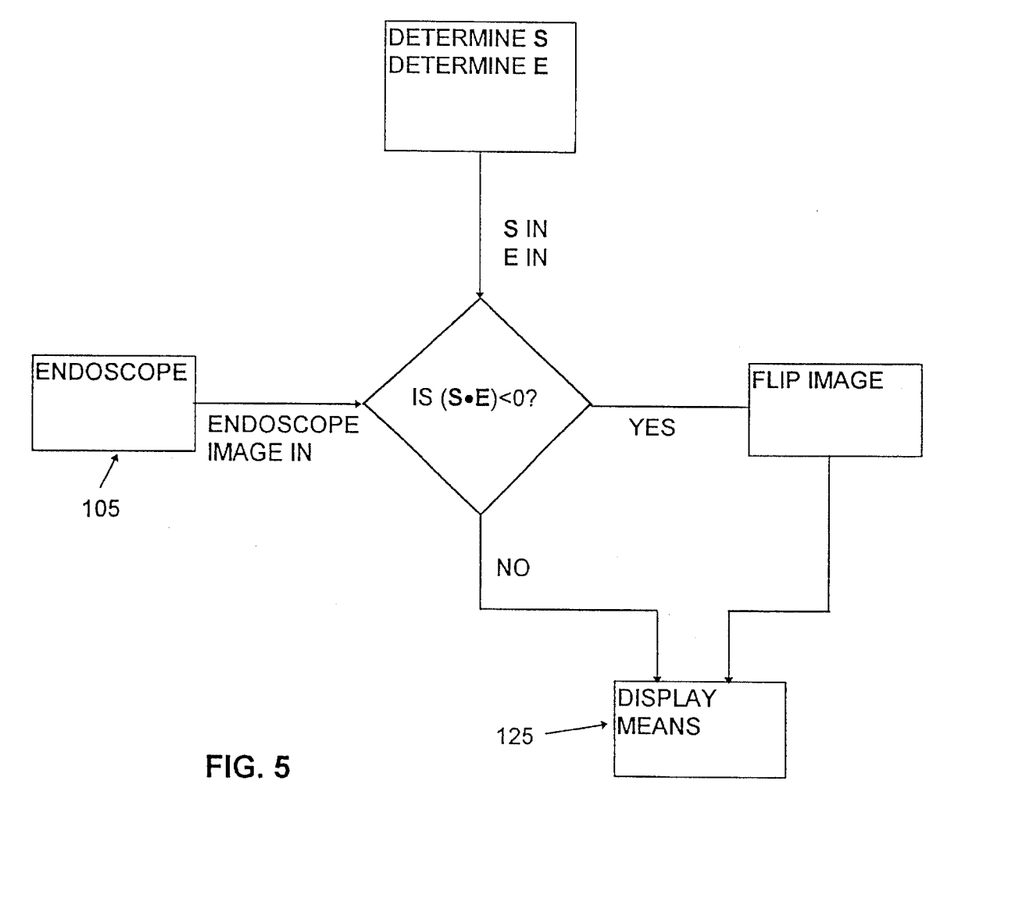
FIG. 5 is a logic diagram illustrating operation of the novel endoscopic viewing system shown in FIG. 3.

Still looking now at FIGS. 3–5, when considering the first preferred embodiment of the invention disclosed in these figures, it has been found that it can be convenient to represent the orientation of surgeon 5 as a vector S, and to represent the orientation of endoscope 105 as a vector E. In this context, it has been observed that when the angle between S and E is less than 90° the surgeon's normal sense of kinesthesia will generally be automatically retained by the endoscopic viewing system. However, it has also been observed that when the angle between S and E exceeds 90°, the surgeon's normal sense of kinesthesia will generally not be automatically retained by the system, and signal processing means 120 must intercede if the surgeon's normal sense of kinesthesia is to be maintained.

Stated mathematically, it has been found that if $$(S \cdot E) > 0$$

then the surgeon's normal sense of kinesthesia will generally be automatically retained by the endoscopic viewing system.

At the same time, however, it has been found that if $$(S \cdot E) < 0$$

then the surgeon's normal sense of kinesthesia will generally not be automatically retained by the endoscopic viewing system.

By way of example, consider the situation shown in FIG. 1. Here one can consider a coordinate system where the vectors S and E are in the form (X,Y,Z), where the X axis extends left to right across the page, the Y axis extends bottom to top along the page, and the Z axis extends out of the page. In such a coordinate system, $$S=(0,1,0)$$

and $$E=(0,1,0)$$

Accordingly, it will be seen that $$(S \cdot E) = 1$$

Since $$(S \cdot E) > 0$$

one would expect from the mathematics that the surgeon's normal sense of kinesthesia will be automatically retained by the endoscopic viewing system. In fact, in the situation shown in FIG. 1, the surgeon's normal sense of kinesthesia is automatically retained by the endoscopic viewing system.

Consider further the situation shown in FIG. 2. Here one can consider $$S=(0,1,0)$$

and $$E=(0,-1,0)$$

Accordingly, it will be seen that $$(S \cdot E) = -1$$

Since $$(S \cdot E) < 0$$

one would expect from the mathematics that the surgeon's normal sense of kinesthesia will not be automatically retained by the endoscopic viewing system. In fact, in the situation shown in FIG. 2, the surgeon's normal sense of kinesthesia is not automatically retained by the endoscopic viewing system.

In the first preferred embodiment of the present invention disclosed in FIGS. 3–5, it has been recognized that whenever $$(S \cdot E) < 0$$

the image obtained from endoscope 105 should be transformed into its mirror image prior to presentation on display means 125. However, so long as $$(S \cdot E) > 0$$

then the image obtained from endoscope 105 can be displayed on display means 125 in exactly the form it is obtained.

To this end, and still looking now at FIGS. 3–5, the outputs from endoscope 105, endoscope tracking means 110 and surgeon tracking means 115 are all connected as inputs to signal processing means 120. The output from signal processing means 120 is in turn connected as the input to display means 125. Signal processing means 120 are configured and programmed so that when $$(S \cdot E) > 0$$

then the video output from endoscope 105 will be applied directly to display means 125, without any transformation. At the same time, however, signal processing means 120 are also configured and programmed so that when $$(S \cdot E) < 0$$

then the video output from endoscope 105 will be "flipped" (i.e., transformed into its mirror image) before being displayed on display means 125. In other words, whenever the angle between S and E exceeds 90°, signal processing means 120 will automatically reconfigure the video output from endoscope 105 so that a mirror image of that output is displayed on display means 125.

The specific apparatus and software necessary for conducting the foregoing analysis and mirror transformation (when appropriate) are of the sort well known in the art.

For example, signal processing means 120 can comprise simple logic for determining the value of (S·E). In addition, signal processing means 120 can comprise a simple video buffer for storing the video signals received from endoscope 105, and appropriate hardware and software for appropriately writing the contents of this buffer to display device 125 according to whether a mirror transformation should be effected or not.

Alternatively, through a hardware modification of the sort well known in the art, a standard monitor can be configured such that the scanning direction of the monitor can be controlled (e.g. reversed) by sending the monitor an appropriate control signal. By way of example, one such monitor might be an appropriately modified Sony PVM-2030 monitor. In such a system, signal processing means 120 can be adapted to send the appropriate control signal for reversing the monitor's normal scanning direction whenever a mirror transformation should be effected.

In yet another alternative, signal processing means 120 can comprise dedicated hardware and software for effecting a mirror transformation when appropriate. For example, signal processing means 125 could include an Abekas A51+ Digital Special Effects System for converting the image actually received from endoscope 105 to its mirror image before sending the converted image to display means 125. The Abekas A51+Digital Special Effects System is commercially available from Abekas Video Systems, Inc. of Redwood City, Calif. 94063.

The foregoing embodiment of the present invention is particularly well suited to those situations where the orientation of endoscope 105 is substantially the same as the orientation of surgeon 5, i.e. where $$(S \cdot E) \approx 1$$

or where the orientation of endoscope 105 is substantially the opposite as the orientation of surgeon 5, i.e., where $$(S \cdot E) \approx -1$$

In these circumstances the present invention is able to maintain the surgeon's normal sense of kinesthesia very well using a relatively simple and inexpensive mirror transformation technique. In addition, since the orientation of the endoscope is substantially parallel to the orientation of the surgeon, the view generated by the viewing system will tend to look fairly accurate from the point of view of the surgeon.

Unfortunately, however, in many situations the orientation of endoscope 105 may not be substantially parallel to the orientation of the surgeon. More particularly, and looking now at FIG. 6, in many circumstances endoscope 105 may extend at a substantial angle to the orientation of surgeon 5. In this case, the images of body structures 15A and 15B and surgical instrument 20 will tend to look distorted when viewed on the monitor by surgeon 5, as will any movement across the surgical site. More specifically, in the example shown in FIG. 6, endoscope 105 is oriented at approximately a 45° angle relative to surgeon 5. In this setting, body structure 15A will appear reduced in size on the monitor and body structure 15B will appear enlarged in size on the monitor. Even more apparently, movement of surgical instrument 20 in a left to right direction across the surgical site is seen as diagonal movement on the monitor.

Figure 6:
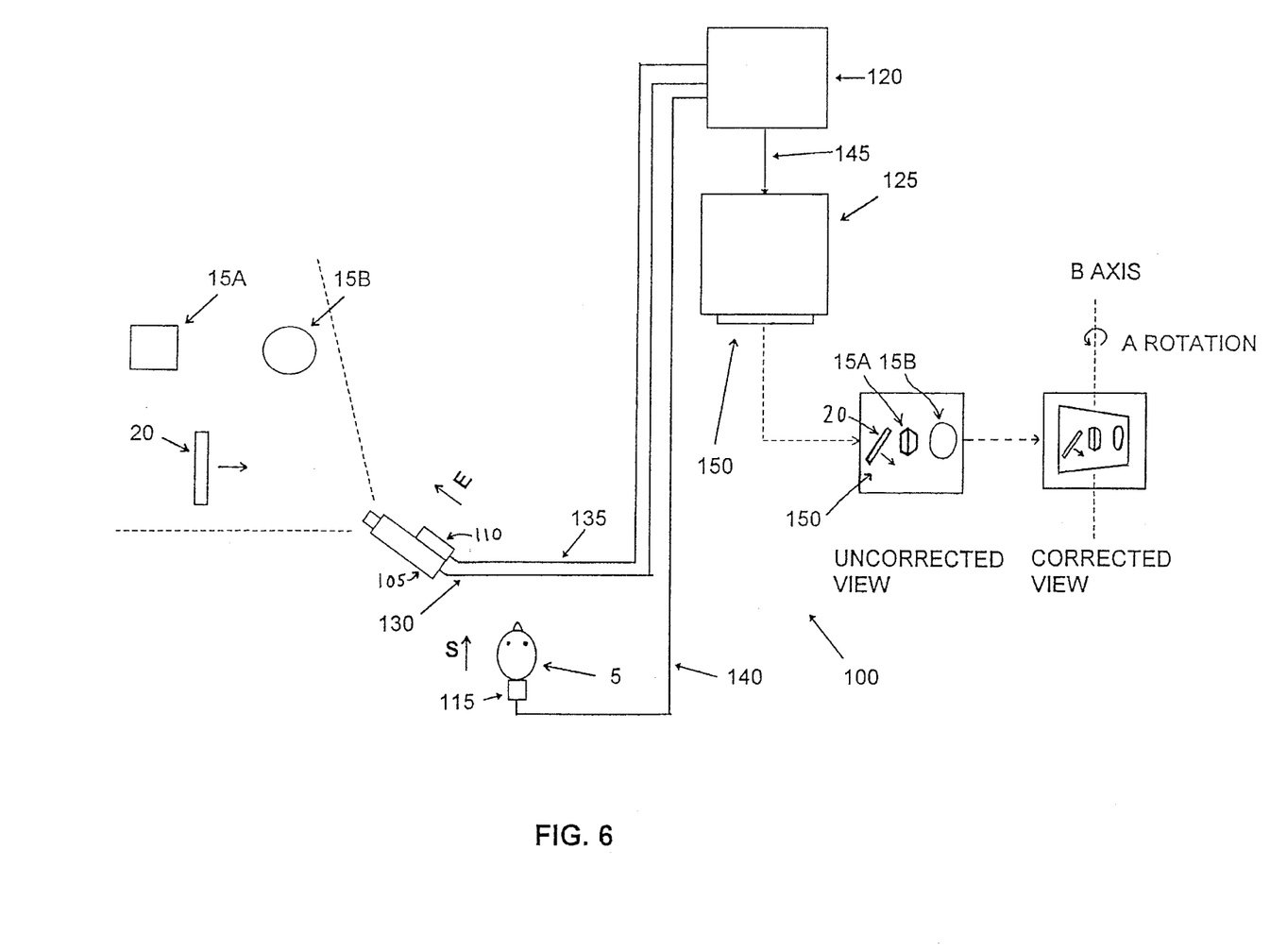
FIG. 6 is a schematic view showing an alternative embodiment for the novel endoscopic viewing system of the present invention.
Figure 7:
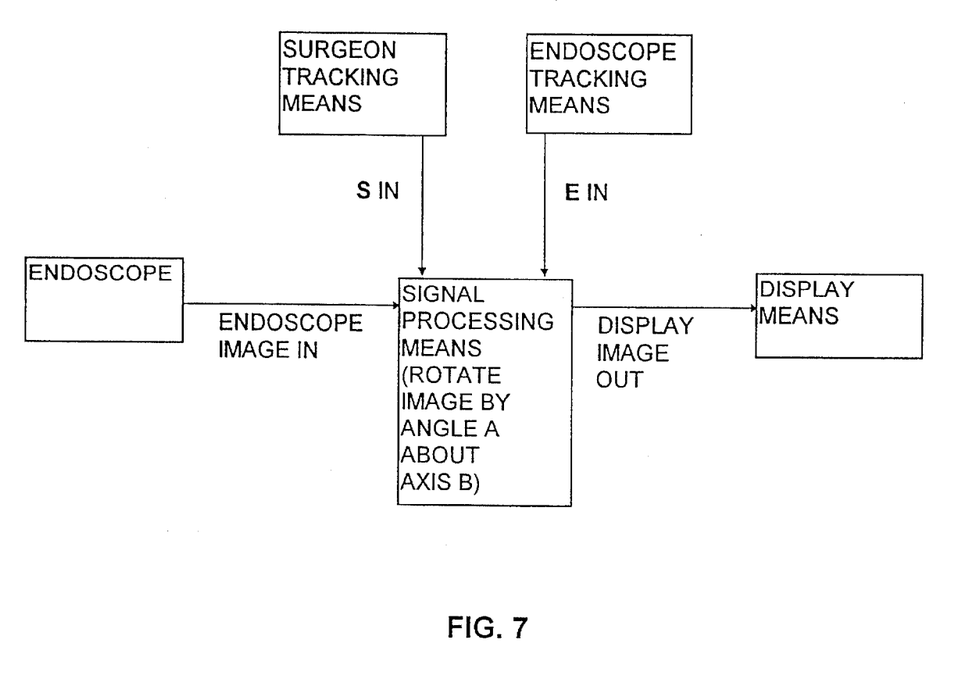
FIG. 7 is a block diagram of the alternative embodiment shown in FIG. 6.

An alternative form of the present invention is adapted to correct for these distortions. More particularly, and looking now at FIGS. 6 and 7, a second preferred embodiment of the present invention will now be described. In this form of the present invention, it has been recognized that if the image captured by endoscope 5 is rotated by a selected angle A about a selected axis B, then the image displayed on display means 125 will be free from the aforementioned distortions. More particularly, it has been recognized that where the normalized vector S represents the orientation of surgeon 5, and the normalized vector E represents the orientation of endoscope 105, then rotating the image captured by endoscope 105 by the angle A, where $$A = arccos(S \cdot E)$$

about the three dimensional axis B, where $$B = (S \times E)$$

will ensure that the image displayed on display means 125 will be free from the aforementioned distortions.

To effect the foregoing transformation, signal processing means 120 are constructed and programmed so as to be capable of determining the angle A and the three dimensional axis B from endoscope tracking means 110 and surgeon tracking means 115. For example, signal processing means 120 can comprise simple logic of the sort well known in the art for determining the value of arccos(S·E) and (S×E). In addition, signal processing means 120 are constructed so as to incorporate a graphics processing engine such as or similar to the Abekas A51+Digital Special Effects System discussed above. With such a system, signal processing means 120 are capable of transforming the image captured by endoscope 105 in the desired manner once the angle A and the three dimensional axis B have been determined by the signal processing means.

As disclosed above, with the invention embodiment of FIGS. 6 and 7, the endoscopic viewing system is adapted to rotate the image captured by endoscope 105 by a selected angle A about a selected three dimensional axis B before presenting that image to the surgeon. More particularly, where the normalized vector S represents the three dimensional orientation of surgeon 5 in the form $(X_s, Y_s, Z_s)$, and the normalized vector E represents the three dimensional orientation of endoscope 10 in the form $(X_E, Y_E, Z_E)$, $$A = arccos(S \cdot E)$$

and $$B=(S\times E)$$

In essence, the foregoing image transformation takes place in three dimensions, due to the three dimensional form of vector S and the three dimensional form of vector E, which together yield a three dimensional form to the vector B (which defines the axis of rotation for the image).

In this respect, however, it has also been recognized that rotating an image about an axis can cause the loss of image information during the image transformation. The extent of this information loss depends on the nature of the rotation involved, among other things. Thus, it is generally preferable to minimize the number and extent of image rotations during image transformation where the information content of the image is important.

In this respect it has also been recognized that in many real world situations, e.g. endoscopic surgical procedures, a person's sense of kinesthesia tends to be much more significant with respect to the X and Y axes than with respect to the Z axis.

With the foregoing in mind, it has been recognized that with the endoscopic viewing system of FIGS. 6 and 7, the system can provide certain additional advantages if the image transformations are conducted only with respect to the X and Y axes. This can be accomplished by projecting the three dimensional vectors S and E into the X-Y plane, and then normalizing them, prior to computing A and B. In other words, where $$S=(X_s, Y_s, Z_s)$$

then the corresponding projected and normalized vector S' is computed as follows:

$$S' = \frac{(X_S, Y_S, 0)}{\|(X_S, Y_S, 0)\|}$$

and where $$E=(X_E, Y_E, 0)$$

then the corresponding projected and normalized vector E' is computed as follows:

$$E' = \frac{(X_E, Y_E, 0)}{\|(X_E, Y_E, 0)\|}$$

The values of A and B are then computed in the normal manner for the system using S' and E' in place of S and E, i.e., $$A=arccos(S'\cdot E')$$

and $$B=(S'\times E')$$

It will, of course, be appreciated that numerous modifications may be made to the foregoing preferred embodiments of the invention without departing from the scope of the present invention.

Thus, for example, while in the foregoing description the invention has been discussed in the context of endoscopic surgical procedures, numerous other contexts of use also are contemplated. For example, the present invention is equally applicable to any situation where an operator must perform tasks at a remote site using extended tools, with the operator visualizing the procedure indirectly through a remote viewing system. Examples of such fields might include nuclear material handling, toxic chemical handling, infectious material handling, closed pipeline work and remote robotic work, to name but a few of the possibilities. In all of these situations the present invention may be advantageously employed. Additionally, the present invention may be employed in situations where the viewing system is to be used principally for inspection purposes.

Furthermore, it is anticipated that endoscope 5 could be replaced with another instrument of the sort adapted to yield a visual representation of the surgical site, e.g. an ultrasound device.

In addition to the foregoing, while in the foregoing description of the invention surgeon tracking means 115 have been described and illustrated as being securely attached to the surgeon 5 so as to directly track the orientation of the surgeon, it is anticipated that surgeon tracking means 115 could also be adapted so as to indirectly track the orientation of the surgeon. By way of example, if the surgeon was viewing the surgical procedure on a head-mounted display which moved automatically with the surgeon, surgeon tracking means 115 might be attached to the head-mounted display rather than to the surgeon. Alternatively, if the surgeon was viewing the surgical site on a boom-mounted monitor, with the monitor being moved about on its boom arm during the procedure as needed so as to always face the surgeon, one could indirectly track the orientation of the surgeon by tracking the orientation of the monitor or its boom arm. In this case surgeon tracking means 115 might be attached to the monitor or its boom arm rather than to the surgeon.

It should also be appreciated that in the foregoing description of the invention, when speaking about the orientation of the endoscope, the intended meaning is not necessarily the same as the longitudinal axis of the endoscope itself. Rather, when speaking about the orientation of the endoscope, what is meant is the direction of view of the endoscope. This distinction becomes more readily apparent when one considers that many endoscopes are arranged so that their direction of view is set at an angle to the longitudinal axis of the endoscope. Furthermore, in the foregoing description of the invention, when speaking about the orientation of the surgeon, the intended meaning is not necessarily the same as the orientation of the surgeon's head. Rather, when speaking about the orientation of the surgeon, what is meant is the orientation of the surgeon relative to the field of interest and/or interaction.

Also, in the foregoing description of the preferred embodiments of the invention, endoscope tracking means are disclosed for tracking the orientation of the endoscope, and surgeon tracking means are disclosed for tracking the orientation of the surgeon. This arrangement provides a convenient system for tracking the relative orientation between the endoscope and the surgeon, and for generating tracking signals representative of the relative orientation between the endoscope and the surgeon. Of course, in some situations the orientation of the endoscope could be substantially fixed, in which case only the orientation of the surgeon needs to be monitored and the endoscope tracking means can be omitted. Alternatively, in some situations the orientation of the surgeon could be substantially fixed, in which case only the orientation of the endoscope needs to be monitored and the surgeon tracking means can be omitted. The important thing for the present invention is that appropriate apparatus be provided for tracking the relative orientation between the endoscope and the surgeon, and for generating tracking signals representative of the relative orientation between the endoscope and the surgeon. The exact form of this tracking apparatus may vary according to the specific conditions at hand.

What is claimed is:

1. An endoscopic viewing system comprising:

an endoscope for capturing a first image of an object and for generating first video signals representative of said first image;

tracking means for determining the relative orientation between said endoscope and a surgeon and for generating tracking signals representative of the relative orientation between said endoscope and said surgeon;

signal processing means connected to said endoscope and said tracking means, said signal processing means being adapted to receive said first video signals from said endoscope and to modify the same as required based on said tracking signals received from said tracking means so as to provide second video signals representative of a second image of said object, wherein said second image of said object is arranged so as to maintain the surgeon's normal sense of kinesthesia during endoscopic surgery regardless of the orientation of said endoscope vis-a-vis said surgeon; and display means connected to said signal processing means for receiving said second video signals from said signal processing means and displaying said second image for viewing by said surgeon.

2. An endoscopic viewing system according to claim 1 wherein said signal processing means are arranged so that whenever said endoscope and said surgeon are oriented in substantially opposite directions, said signal processing means will flip said first image of said object about an axis when creating said second image of said object, whereby said second image of said object will be a mirror image of said first image of said object.

3. An endoscopic viewing system according to claim 1 wherein said signal processing means are arranged so that they will create said second image of said object by rotating said first image of said object about an axis, with the degree of rotation being determined by the relative orientation of said endoscope vis-a-vis said surgeon.

4. An endoscopic viewing system according to claim 3 wherein the axis of rotation is determined by the relative orientation of said endoscope vis-a-vis said surgeon.

5. An endoscopic viewing system comprising:

an endoscope for capturing a first image of an object and for generating first video signals representative of said first image;

endoscope tracking means for determining the orientation of said endoscope and for generating first tracking signals representative of the orientation of said endoscope;

surgeon tracking means for determining the orientation of a surgeon and for generating second tracking signals representative of the orientation of said surgeon;

signal processing means connected to said endoscope, said endoscope tracking means and said surgeon tracking means, said signal processing means being adapted to receive said first video signals from said endoscope and to modify the same as required based on said first tracking signals and said second tracking signals so as to provide second video signals representative of a second image of said object, wherein said second image of said object is arranged so as to maintain the surgeon's normal sense of kinesthesia during endoscopic surgery regardless of the orientation of said endoscope vis-a-vis said surgeon; and display means connected to said signal processing means for receiving said second video signals from said signal processing means and displaying said second image for viewing by said surgeon.

6. A method for maintaining a surgeon's sense of kinesthesia during endoscopic surgery regardless of the orientation of the endoscope vis-a-vis the surgeon, said method comprising:

(1) providing an endoscopic viewing system comprising:

an endoscope for capturing a first image of an object and for generating first video signals representative of said first image;

tracking means for determining the relative orientation between said endoscope and a surgeon and for generating first tracking signals representative of the relative orientation between said endoscope and said surgeon;

signal processing means connected to said endoscope and said tracking means, said signal processing means being adapted to receive said first video signals from said endoscope and to modify the same as required based on said tracking signals received from said tracking means so as to provide second video signals representative of a second image of said object, wherein said second image of said object is arranged so as to maintain the surgeon's normal sense of kinesthesia during endoscopic surgery regardless of the orientation of said endoscope vis-a-vis said surgeon; and display means connected to said signal processing means for receiving said second video signals from said signal processing means and displaying said second image for viewing by said surgeon;

(2) generating said first video signals and said tracking signals and transmitting the same to said signal processing means;

(3) processing said first video signals so as to generate second video signals;

(4) transmitting said second video signals to said display means; and (5) displaying said second image represented by said second video signals on said display means.

7. A method according to claim 6 wherein said signal processing means are arranged so that they will create said second image of said object by rotating said first image of said object about an axis, with the degree of rotation being determined by the relative orientation of said endoscope vis-a-vis said surgeon.

8. A method according to claim 7 wherein the axis of rotation is determined by the relative orientation of said endoscope vis-a-vis said surgeon.

9. A method according to claim 6 wherein said signal processing means are arranged so that whenever said endoscope and said surgeon are oriented in substantially opposite directions, said signal processing means will flip said first image of said object about an axis when creating said second image of said object, whereby said second image of said object will be a mirror image of said first image of said object.

10. A method for maintaining a surgeon's sense of kinesthesia during endoscopic surgery regardless of the orientation of the endoscope vis-a-vis the surgeon, said method comprising:

(1) providing an endoscopic viewing system comprising:

an endoscope for capturing a first image of an object and for generating first video signals representative of said first image;

endoscope tracking means for determining the orientation of said endoscope and for generating first tracking signals representative of the orientation of said endoscope;

surgeon tracking means for determining the orientation of a surgeon and for generating second tracking signals representative of the orientation of said surgeon;

signal processing means connected to said endoscope, said endoscope tracking means and said surgeon tracking means, said signal processing means being adapted to receive said first video signals from said endoscope and to modify the same as required based on said first tracking signals and said second tracking signals so as to provide second video signals representative of a second image of said object, wherein said second image of said object is arranged so as to maintain the surgeon's normal sense of kinesthesia during endoscopic surgery regardless of the orientation of said endoscope vis-a-vis said surgeon; and display means connected to said signal processing means for receiving said second video signals from said signal processing means and displaying said second image for viewing by said surgeon;

(2) generating said first video signals, said first tracking signals and said second tracking signals and transmitting the same to said signal processing means;

(3) processing said first tracking signals and said second tracking signals so as to determine the orientation of said endoscope and the orientation of said surgeon, assigning the vector E to the orientation of said endoscope and the vector S to the orientation of said surgeon, and then calculating $$A = \arccos(S \cdot E)$$

and $$B = (S \times E);$$

(4) processing said first video signals so as to generate second video signals corresponding to said first image rotated about vector B by the angle A;

(5) transmitting said second video signals to said display means; and (6) displaying said second image represented by said second video signals on said display means.

11. A method according to claim 10 wherein vector S and vector E are projected into the X-Y plane and then normalized prior to calculating A and vector B.

12. A viewing system comprising:

a sensor for capturing a first image of an object and for generating first video signals representative of said first image;

tracking means for determining the relative orientation between said sensor and a viewer and for generating tracking signals representative of the relative orientation between said sensor and said viewer; and signal processing means connected to said sensor and said tracking means, said signal processing means being adapted to receive said first video signals from said sensor and to modify the same as required based on said tracking signals received from said tracking means so as to provide second video signals representative of a second image of said object, wherein said second image of said object is arranged so as to maintain the viewer's normal sense of kinesthesia during a procedure involving the object regardless of the orientation of said sensor vis-a-vis said viewer;

said signal processing means being adapted to be connected to display means whereby said second image of said object can be displayed to said viewer.

* * * * *